United States Patent
Van Bekkum

(10) Patent No.: US 10,274,355 B2
(45) Date of Patent: Apr. 30, 2019

(54) DENSITY COMPENSATION FOR ELECTROMECHANICAL LIQUID LEVEL GAUGES

(71) Applicant: Honeywell International Inc., Morristown, NJ (US)

(72) Inventor: Frank Van Bekkum, Bergschenhoek (NL)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 851 days.

(21) Appl. No.: 14/875,325

(22) Filed: Oct. 5, 2015

(65) Prior Publication Data

US 2017/0097253 A1    Apr. 6, 2017

(51) Int. Cl.
| | |
|---|---|
| *G01F 23/32* | (2006.01) |
| *G01F 23/00* | (2006.01) |
| *G01N 9/18* | (2006.01) |
| *G01N 9/12* | (2006.01) |
| *G01F 25/00* | (2006.01) |

(52) U.S. Cl.
CPC ...... *G01F 23/0023* (2013.01); *G01F 23/0076* (2013.01); *G01N 9/12* (2013.01); *G01N 9/18* (2013.01); *G01F 25/0061* (2013.01)

(58) Field of Classification Search
CPC .................................................. G01F 23/0023
See application file for complete search history.

(56) References Cited

U.S. PATENT DOCUMENTS

| | | | |
|---|---|---|---|
| 2,791,906 A * | 5/1957 | Vetter ...................... | G01F 23/14 |
| | | | 73/291 |
| 3,393,061 A * | 7/1968 | Augustin ................ | C03B 18/16 |
| | | | 65/182.5 |
| 4,471,656 A | 9/1984 | Sanders et al. | |
| 4,786,846 A * | 11/1988 | Uchida ................... | G01F 23/46 |
| | | | 318/482 |
| 5,806,363 A | 9/1998 | Khoi et al. | |
| 8,997,549 B2 | 4/2015 | Joosten et al. | |
| 2009/0266178 A1 | 10/2009 | Matzoll, Jr. et al. | |
| 2013/0269432 A1 | 10/2013 | Brutschin et al. | |

FOREIGN PATENT DOCUMENTS

DE    102009060866 A1    7/2011

* cited by examiner

*Primary Examiner* — Son T Le
*Assistant Examiner* — Alex T Devito
(74) *Attorney, Agent, or Firm* — Jetter & Associates, P.A.; Neil R. Jetter

(57) ABSTRACT

A method of measuring liquid level in a tank. An electromechanical liquid level gauge (ESG) is provided including a processor, a displacer suspended on a wire from a grooved drum having a servo motor coupled thereto to rotate the drum for balancing the displacer. A change in liquid level causes a change in a counterforce to move the ESG out of balance. The processor monitors a torque sensor output, and controls movement of the motor using a programmed apparent weight (AW) setpoint to raise or lower the displacer based on an AW derived from the torque. An associated memory stores a density compensated fixed immersion depth level gauging algorithm. The algorithm implements obtaining a density reading for the liquid, continuously corrects an immersion depth of the displacer for changes in density to provide an essentially fixed immersion depth, and calculates the liquid level from the density reading and immersion depth.

13 Claims, 3 Drawing Sheets

DENSITY COMPENSATION FOR ELECTROMECHANICAL LIQUID LEVEL GAUGES

FIELD

Disclosed embodiments relate to electromechanical liquid level gauges that use the servo principle.

BACKGROUND

Electromechanical liquid level servo gauges (ESGs) are used for the accurate measurement of product level and the water interface level in bulk storage tanks used for typical hydrocarbons (often referred to as fuel and oil) and a variety of other liquid chemicals. These products range from very light chemicals, like so called LPG's (mixtures of propane and butane or even liquefied natural gas (LNG)) to all types of refined products such as naphtha, gasoline, diesel, jet fuels, lubricants and all types of chemicals, both pure and mixed.

The servo principle is based on the measurement of the apparent weight of a displacer that is within the tank. The displacer is a mechanical body suspended on a strong thin measuring wire, where the displacer material has a higher density than the liquid to be measured. The measurement wire is wound on a high accuracy machined grooved drum with a calibrated circumference. The apparent weight resulting from the weight of the displacer minus the weight of the displaced liquid product is measured and is then used by a computing device such as a microcontroller with the servo motor used to rotate drum in order to position the displacer at a different height in the tank.

By rotating the drum the wire is spooled up or paid out into the tank and the displacer is raised or lowered until the measured apparent weight equals the programmed set point. For safety reasons typically a magnetic coupling (using pole pairs) may be located between drum and electronics (motor, microcontroller, electronics, etc.) as many of the liquids products which are commonly stored in bulk storage tanks are flammable and typically need an explosion safe design. The displacer being more dense than the density of the product in the tank is basically kept at the same level using Archimedes law which indicates that the upward buoyant force that is exerted on a body immersed in a fluid, whether fully or partially submerged, is equal to the weight of the fluid that the body displaces.

The apparent weight resulting from the displaced liquid is dependent on the density of the displaced liquid and the amount of the displaced liquid. The amount of the displaced liquid depends again on the shape of the displacer, and the set point (i.e. how much weight there needs to be displaced).

Vapor influence, caused by dense vapors, especially on products with low dielectric constant and a relative high dipole moment result in accuracy limiting physics, which make radar unsuitable and unacceptable for legal metrology use. The large variation in saturation which are not predictable also makes it generally not possible to compensate for these vapor effects, which especially occur with light hydrocarbons and chemicals, where ESGs do not have these limitations. Some examples are LPGs, ethanol and multiple industrial solvents. Also foam is an example where an ESG still can detect the liquid surface while radar will generally not find any reflection. This means that ESGs are still an important and much relied upon accurate measurement technology, especially when high and certified accuracy is a needed, such as for custody transfer applications.

SUMMARY

This Summary is provided to introduce a brief selection of disclosed concepts in a simplified form that are further described below in the Detailed Description including the drawings provided. This Summary is not intended to limit the claimed subject matter's scope.

Disclosed embodiments recognize one limitation of conventional electromechanical liquid level servo gauges (ESGs) is the significant sensitivity of the level measurement with respect to liquid density variations. Although this effect can be minimized by selecting displacers with a relatively large cross sectional area, this is often not possible due to installation limitations such as small area tank nozzles or obstructed tank access. Hence smaller diameter displacers are typically preferred. The density sensitivity of ESGs thus poses problems for the use for custody transfer and legal metrology when high and certified accuracy is a needed, especially when products are often changed or have a wide variance in composition and/or purity.

Disclosed embodiments solve these problems by providing ESGs which include automatic and continuous compensation for density changes of liquid products (density compensation) in bulk storage tanks, such as for storing hydrocarbon fuels or a variety of other liquid chemicals. Discloses level sensing does not work with a conventional spring or contraweight, but instead with a programmed software-based apparent weight (AW) setpoint. This setpoint is compared with the measured AW and the processor in response commands raising or lowering the displacer.

One disclosed embodiment comprises a method of measuring liquid level in a tank. An ESG is provided including processor, a displacer suspended on a thin and strong measuring wire from a precision grooved drum having a servo motor coupled thereto for rotating the drum for balancing the displacer. A change in the liquid level causes a change in a counterforce to move the ESG out of balance. The processor monitors an output from torque sensor which senses the torque on the drum, and controls a movement of the motor using a programmed AW setpoint to raise or lower the displacer based on a current measured AW value derived from the torque.

The processor has an associated memory which stores a density compensated fixed immersion depth level gauging algorithm (algorithm). The algorithm implements obtaining a density reading for the liquid, continuously correcting an immersion depth of the displacer for changes in the density to provide an essentially fixed immersion depth, and calculating the liquid level from both the density reading and the immersion depth to provide a density compensated liquid level measurement.

To obtain the density reading the density can be measured using the displacer and Archimedes law, or a known displacer shape can be used with briefly submerging and/or raising the displacer and using the known displacer shape to estimate the actual density. The density can also be obtained from another method without the need for displacer shape, such as determined externally, for example from a Hybrid Inventory Management System (HIMS). HIMS is a hybrid density measurement technique where a pressure transmitter is used to measure the hydrostatic head (from a pressure

DETAILED DESCRIPTION

Figure 1:
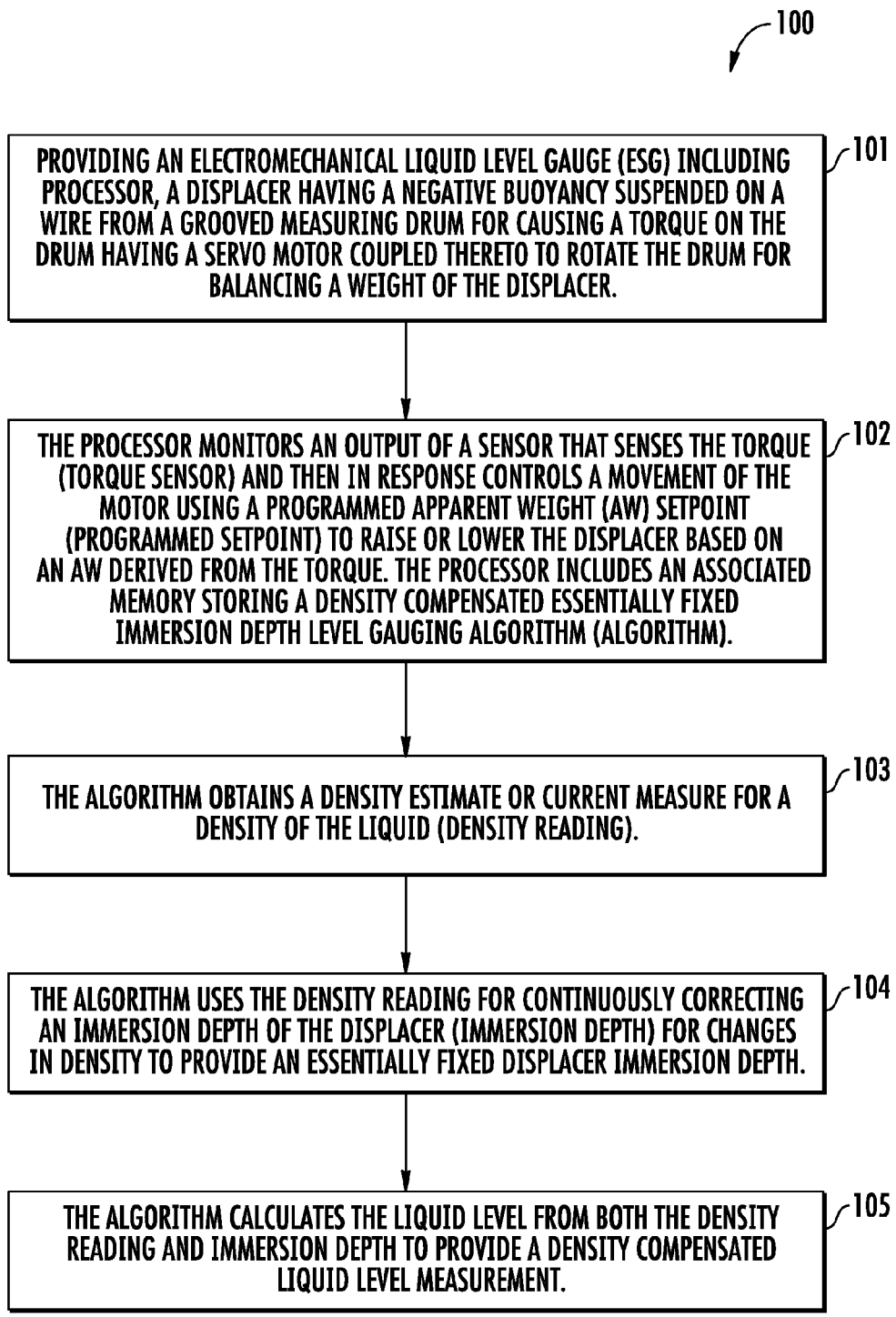
FIG. 1 is a flow chart that shows steps in a method of automatic density compensated liquid level measurement using an ESG, according to an example embodiment.

Disclosed embodiments are described with reference to the attached figures, wherein like reference numerals are used throughout the figures to designate similar or equivalent elements. The figures are not drawn to scale and they are provided merely to illustrate certain disclosed aspects. Several disclosed aspects are described below with reference to example applications for illustration. It should be understood that numerous specific details, relationships, and methods are set forth to provide a full understanding of the disclosed embodiments.

One having ordinary skill in the relevant art, however, will readily recognize that the subject matter disclosed herein can be practiced without one or more of the specific details or with other methods. In other instances, well-known structures or operations are not shown in detail to avoid obscuring certain aspects. This Disclosure is not limited by the illustrated ordering of acts or events, as some acts may occur in different orders and/or concurrently with other acts or events. Furthermore, not all illustrated acts or events are required to implement a methodology in accordance with the embodiments disclosed herein.

Disclosed embodiments recognize for ESGs the cross sectional area of the displacer is a significant design criteria, since the liquid density depends on the application, as does the set point (i.e. how much weight needs to be displaced). Although there are many different shapes for displacers, the most important aspect for the density measurement is generally the cross sectional area of the displacer. For simplification it is assumed in this detailed description that the displacer is a pure cylinder in shape, but it is understood in real applications the displacer generally has at least have a top and bottom cone shape.

FIG. 1 is a flow chart that shows steps in a method 100 of automatic density compensated liquid level measurement for a material in a storage tank using an ESG, according to an example embodiment. The tank can represents any suitable structure for receiving and storing at least one liquid or other material (e.g., a powder). The tank can, for example, represent an oil storage tank or a tank for storing other liquid(s) or other material(s). The tank can also have any suitable shape and size. Further, the tank can form part of a larger structure. The larger structure can represent any fixed or movable structure containing or associated with one or more tanks, such as a movable tanker vessel, railcar, or truck or a fixed tank farm.

Step 101 comprises providing an ESG including processor, a displacer having a negative buoyancy suspended on a measuring wire from a grooved measuring drum for causing a torque on the drum having a servo motor coupled thereto to rotate the drum for balancing a weight of the displacer. An equilibrium condition exists when the displacer is partly submerged in the liquid, where a change in the liquid level causes a change in a counterforce to move the ESG out of balance.

In step 102 the processor monitors an output of a torque sensor which senses a torque on the drum and then in response the processor controls a movement (position, speed and direction) of the motor using a programmed AW setpoint (programmed setpoint) to raise the displacer if an AW derived from the torque on the drum is too low or to lower the displacer if the AW is too high to reach the programmed AW setpoint. The processor includes an associated memory storing a disclosed density compensated essentially fixed immersion depth level gauging algorithm (algorithm). The torque sensor can convert the torque signal into a frequency (f) that is coupled to the processor which functions as a Servo Processor Unit (SPU).

Step 103 comprises the algorithm executed by the processor obtaining a density estimate or current measure for a density of the liquid (density reading). As described above, the density can be measured using the displacer and Archimedes law, or a known displacer shape can be used with briefly submerging and/or raising the displacer and using the known displacer shape to estimate the actual density. The density can also be obtained from another method, such as determined externally, for example from a HIMS.

Regarding density determination by submersion vs. dipping, using the displacer 235 the density can be determined by either lowering or raising the displacer 235 into the liquid product in the tank. As the shape of the displacer 235 is generally known, the AW change can be used to assess the density. Alternatively the displacer 235 can be submerged completely into the product. This will take more time, but can result in a higher accuracy. Each method has advantages and disadvantages and the method used could be configured as selectable to provide a fixed method, but the method can also be selected automatically depending on product properties (for example risk of contamination or product built-up), or for example previous data, i.e. density trend, or density variations.

As noted above, instead of determining the liquid density using the displacer shape it is also possible to use external information to determine the density. This external information can comprise:

i) Operator data, such as after the product is sampled and analyzed;
ii) Data from the associated distributed control system (DCS), for example obtained from flow computers, density probes, gas chromatographs, etc. The DCS can load the data into the ESG, or
iii) Data from a HIMS. This is a measurement method typically integrated in the same gauge using a pressure transmitter at the bottom of the tank. The measured hydrostatic head pressure is used together with the measured product level to calculate the product density. HIMS is relative low investment and provides a generally accurate real-time density value, helpful to recalculate the servo set point continuously.

Step 104 comprises the algorithm using the density reading for continuously correcting an immersion depth of the displacer (immersion depth) for changes in density to provide an essentially fixed displacer immersion depth. Step 105 comprises the algorithm calculating the liquid level from both the density reading and immersion depth to provide a density compensated liquid level measurement.

Regarding operation of a disclosed ESG, the amount of displaced liquid displaced by a displacer roughly equals the cross-sectional area of the displacer, multiplied by the immersion depth defined as being how deep the displacer is immersed in the liquid product, times the density of the liquid. As the controller (e.g., microcontroller) of the ESG controls essentially the exact position of the displacer in the tank, the controller will keep the AW (equal to the displacer weight in air minus the weight of the displaced liquid) constant.

As result the immersion depth of the displacer will be constant or semi-constant. As the controller continuously computes how much the displacer is raised and lowered it can calculate the product level in the tank. The immersion depth is however only roughly constant, because when the actual liquid density changes in the tank, and even more particularly in the upper layer of the tank, the immersion depth will vary.

An equation for the AW=the displacer's weight in air (DW)−buoyancy. The buoyancy equals the immerged/submerged volume times the density of the liquid. If the displacer is submerged completely the buoyancy equals the displacer volume (DV) times the density of the liquid (DL), or: Buoyancy=DV*DL. If the displacer is close to the liquid surface and only partially submerged (i.e. immersed) the equation for the apparent weight is:

$$AW=DW-pDV*DL \text{ (with } pDV \text{ as the partial volume).}$$

Hence:

$$DL=(AW-DW)/pDV$$

It is noted that the same equation can be used when the displacer is completely submerged, in which case pDV=DV.

Assuming the ESG is operating to establish the level as accurately as possible, the displacer will operate within its cylindrical part. Accordingly, the partial displaced volume equals:

$$pDV=I*\pi*R*R.$$

where: I=immersion of displacer, R=radius of displacer (as measured in the cylindrical part of the displacer).

For the AW: $AW=DW-I*\pi*R*R*DL$.

Since the processor will keep the AW equal to the programmed AW setpoint, and DW and R are constant, one can observe that if the liquid density changes by x %, the immersion has to change by −x % (again assuming the displacer operates in the cylindrical displacer part). This sensitivity for density changes is a significant advantage for disclosed ESG's.

Assuming the processor has information regarding the displacer shape and dimensions, it can apply a density correction of the indicated liquid level. This allows the ESG to move less and reduce wear and tear. It is also possible to calculate the liquid density when the shape of the displacer is known. If one waits until the product level is stable (this can take several hours after a transfer into the tank, and less after a transfer out of the tank) the processor can lower (or raise) the displacer a known distance. Out of this difference, the liquid density can be calculated.

Although the torque is measured by electronics, it need not be measured directly. In typical applications one may not want to have the sensitive measurement electronics in the same space as where the product and product vapors are. To isolate the sensitive measurement electronics, the torque sensor can include a magnetic coupling formed by two coaxial magnets located between the drum and motor.

Figure 2A:
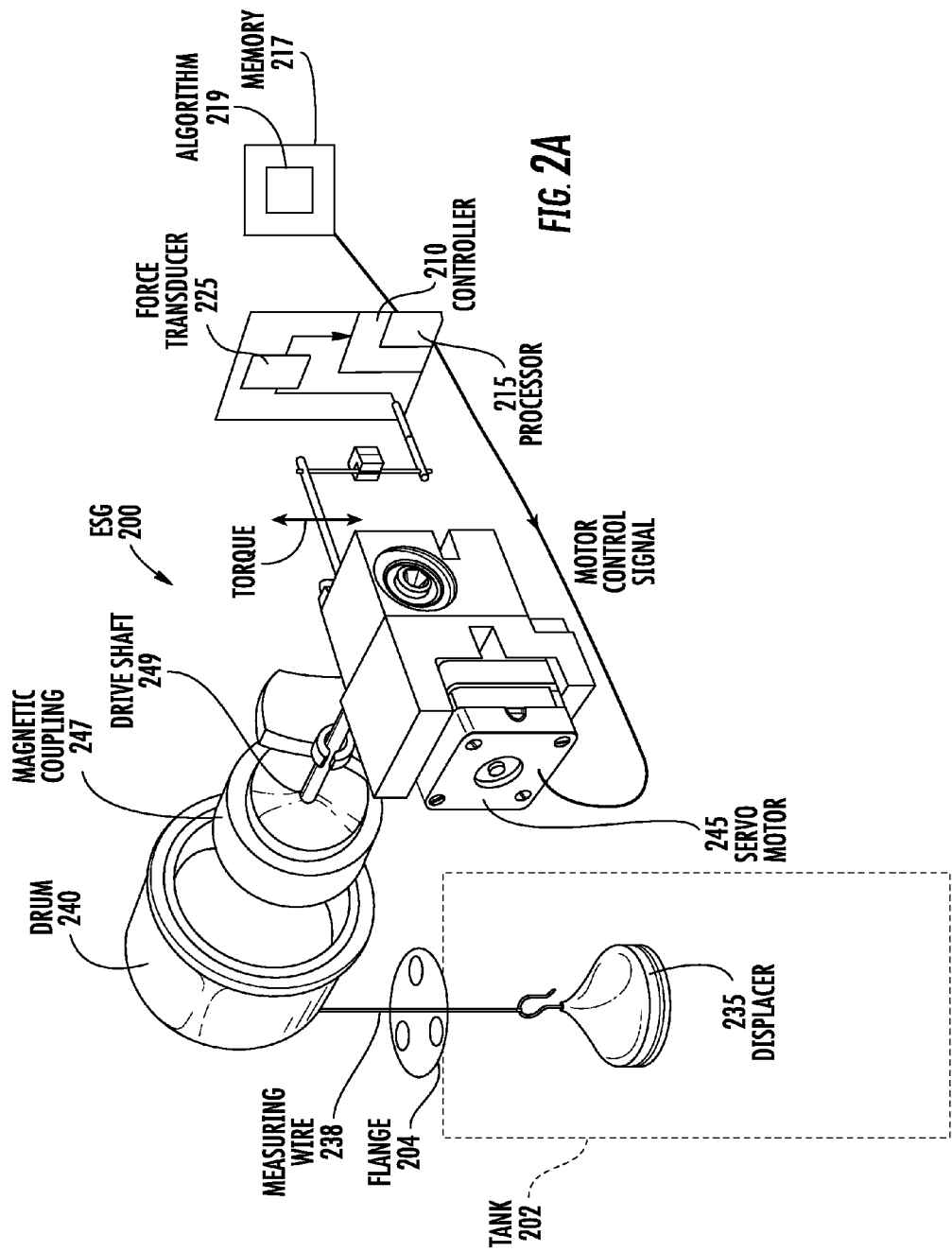
FIG. 2A is a depiction of an example ESG implementing automatic density compensated liquid level measurement, according to an example embodiment.

FIG. 2A shows an example ESG 200 that includes a controller 210 comprising a processor 215 having an associated memory 217 storing a density compensated essentially fixed immersion depth level gauging algorithm (algorithm) 219 programmed to implement the algorithm, according to an example embodiment. The processor 215 can comprise a microprocessor, microcontroller, field programmable gate array, digital signal processor, or other processing or control device.

A force transducer 225 is shown on a common PCB board with the processor 215. The force transducer 225 can convert a torque on the drum 240 into frequency (f) that is coupled to an input of the controller 210 acting as a Servo Processor Unit (SPU) which renders a torque measurement.

ESG 200 includes a displacer 235 within a tank 202 that has a flange 204. The displacer 235 is suspended on a measuring wire 238 from a drum 240 that extends through the flange 204 for causing a torque on the drum 240. The displacer shape and displacer dimensions are generally known. A servo motor with a gear (servo motor) 245 is coupled by a drive shaft 249 to rotate the drum 240 to balance a weight of the displacer 235 in the tank 202 having a liquid therein (not shown). An equilibrium condition exists when the displacer 235 is at a top surface of the liquid, wherein a change in the liquid level causes a change in a counterforce to move the ESG 200 out of balance. As noted above, although not shown, any force which acts via the measuring wire 238 on the drum 240 sensed by force transducer 225 can be transferred as a torque to processor side of the ESG 200 using a magnetic coupling 247.

Figure 2B:
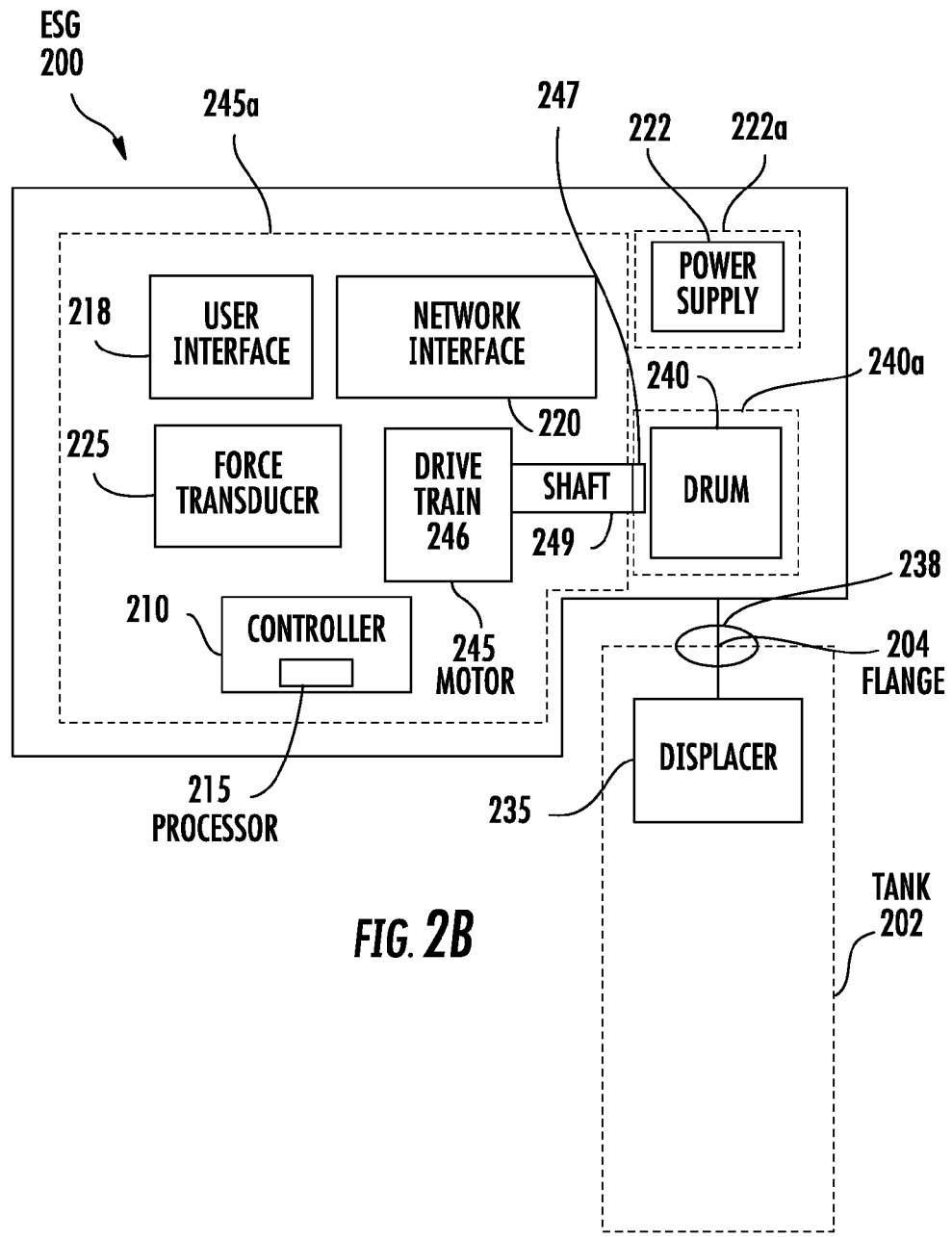
FIG. 2B is a block diagram of an example ESG implementing automatic density compensated liquid level measurement, according to an example embodiment.

FIG. 2B is a block diagram illustration of an example ESG 200, according to an example embodiment. As shown in FIG. 2B, the ESG 200 can included three compartments, a drum compartment 240a, a drive compartment 225a, and a power supply compartment 222a. The drum compartment 240a includes the drum 240 on which a wire 238 is wound. The drum 240 can be rotated in one direction by the drive compartment 245a to lower the displacer 235, and the drum 240 can be rotated in another direction by the drive compartment 245a to raise the displacer 235. The drum 240 includes any suitable structure for raising and lowering the displacer 235 via rotation.

The drive compartment 245a includes a motor 245 including a drive train 246, which imparts rotation to the drum 240 via a shaft 249. For example, the drive train 246 or shaft 249 could generate a magnetic field, and a magnetic coupling 247 can be used to convey torque between the shaft 249 and the drum 240. In these embodiments, no direct connection may be needed between the drum compartment 240a and the other compartments 245a, 222a. However, other techniques for causing rotation of the drum 240 can be used, such as when the shaft 249 is physically connected to the drum 240. The drive train 246 includes any suitable structure for imparting rotation to the drum 240. In particular embodiments, the drive train 246 comprises a stepper motor that causes the drum 240 to rotate in specified steps, meaning the drum 240 does not rotate freely but instead in defined amounts or "steps." Each step of the motor 245 should therefore impart a known amount of rotation to the drum 240. In these embodiments, since the drum 240 has a known diameter or circumference, the length of connector the wire 238 that is dispensed or collected during a single step rotation can be known with a high degree of certainty.

The drive compartment 245a also includes a force transducer 225 which identifies the torque induced on the drum 240 by the weight of displacer 235. When the displacer 235 is dangling from the wire 238, the measured torque is higher.

When the displacer 235 is completely or partially submerged in the material in the tank, the measured torque is lower. The force transducer 225 generally identifies the torque on the drum 240 by measuring the torque on the shaft 249.

ESG 200 is shown including a user interface 218 and a network interface 220 in the drive compartment 245a. The user interface 218 facilitates communications between the ESG 200 and an operator or other plant personnel. The user interface 218 can provide data from an operator to the controller 210, such as a command to initiate level measurements, a command to raise or lower the displacer 235, or a command to enable or disable testing of the ESG 200. The user interface 218 can also allow the personnel to review measurement data generated by the ESG 200. The user interface 218 includes any suitable interface for interacting with one or more users, such as a keypad or keyboard and a display.

The network interface 220 facilitates the communication of data to or from the ESG 200. For example, the network interface 220 could receive level measurements calculated by ESG 200 and transmit the level measurements to one or more external destinations (such as the force transducer 225). The network interface 220 includes any suitable structure supporting wired or wireless communications, such as an Ethernet interface, an RF transceiver, or other wired or wireless interface.

The power supply compartment 222a includes a power supply 222, which provides operating power for the ESG 200. The power supply 222 can provide power to various components of the drive compartment 245a. Depending on the implementation, the power supply 222 may or may not supply power to the drum compartment 240a. The power supply 222 can include any suitable structure for providing power, such as a battery, fuel cell, or solar cell.

As describes below, a significant advantage of disclosed ESGs is the reduction in the sensitivity of density changes on the measured liquid level. Additional advantages include automatic density compensation for level measurements which allows the use of smaller diameter displacers that in turn allows installation on smaller tank nozzles, increased accuracy of the level measurement, and extending the range of density for legal metrology and custody transfer applications, only needing the addition of a disclosed algorithm. A further advantage is the ability for continuous measured density to be correlated with the shape of the displacer to provide enhanced diagnostic information enabling preventive maintenance (detecting displacer contamination), and increased safety.

Reducing the need for ESG movements provided by electronic correction as described above has several advantages, including longer lifetime for the ESG as automatic level adjustments reduce motor wear, and lower power consumption which can be important when for example working on solar power. Instead of conventionally continuously recalculating the setpoint and trying to keep the immersion depth of the displacer constant (using the motor to rotate the measuring drum), it is also possible perform a virtual (electronic) correction to the level reading. The same method can even be used to reduce normal servo movements as result of normal level changes. Also these small changes can be calculated as correction factor. As result part of the control loop can be virtual, and the typical 'hunting' like movement, which can occur as result of noise and small ripple effects will not cause excessive motor movements. This reduces wear and tear on the motor, bearings and the worm reduction gear, used to drive the drum.

Faster response is also provided as compared to a conventional servo gauge design where the gauge has first to move the displacer. The possibility to use a mechanical drive with lower resolution is also provided (for known servo gauges there is a need to be able to step with a fraction of a mm), and this is generally no longer needed as the additional sensitivity can be electronically calculated using disclosed ESGs.

One can also check for contamination (sticky) product on the displacer (e.g., some product polymerized in the tank on the displacer) by creating a reference buoyancy curve (under known non-contaminated conditions) and later comparing a measured buoyancy curve to the reference buoyancy curve. To create a buoyancy curve, a volume function as function of the immersion depth can be used, or this can be calculated from area or diameter of the displacer as function of immersion. If the product sticks to the displacer, it will cause a different AW at various immersion depths, as it will cause additional buoyancy when the sticky product is immersed, so that the measured buoyancy curve will not match to the reference buoyancy curve.

Other diagnostic tools provided include:

Trending of density in top layer of product can be performed in the system. The system can be a DCS, a personal computer (PC)-based system or supervisory control and data acquisition (SCADA) system package. A disclosed algorithm can periodically (for example one per minute, or once per half-hour) retrieve the most recent density value established using the AW measurement and displacer shape. The trend could then be used to provide the operator with additional information. The data can be displayed as graph with additional enhancements such as temperature correction to a reference standard (in the Oil & Gas industry it is common to refer density and volume back to either 60° F., 15° C. or 20° C., depending on the geographical location), density alarms and audit trail (e.g., a sudden change in density could indicate product contamination, such as light product has entered into the tank.

Establishing the statistic variance and distribution of density over time (with variable time scale benefits), and generating a warning when excessive densities are noted after loading as this can be precursor warning to product contamination. During periods of inactivity trends can be an indicator of need for maintenance.

Besides density determination it is also possible to automatically detect the displacer shape, even with unknown density. When looking at the previous shown different displacer shapes, it should be clear that a qualifying parameter and unique for each displacer could be for example the height of the cylindrical parts and the total height of the displacer. Automatic displacer shape detection can be used to simplify commissioning, detecting displacer contamination (adhering product), etc.

Density verification scheduling can also be provided. An important part of the mechanism can be the scheduling of the density information (except if the density is fed from external systems or obtained from for example HIMS, as described above). Density changes are most likely to occur after loading of the tank, after long periods as result of which weathering (aging) can occur, as result of large temperature changes of the liquid or gas temperature (diurnal temperature) effects. At the same time density changes during loading and unloading are of less importance, as the exact level determination during pumping is any how less critical. While when the product level is stable (i.e. quiet) the need for density determination can be minimized to once every couple of hours.

On the other side, density changes after the tank has been loaded are to be expected, especially when receiving large batches or when the tank is refilled completely, possibly with a different product and/or batch. As result a predictive density scan scheduling can be used which uses the above 'cases' to establish when there is a need for a new (updated) density measurement.

EXAMPLES

Disclosed embodiments are further illustrated by the following specific Examples, which should not be construed as limiting the scope or content of this Disclosure in any way.

As described above, disclosed level sensing does not work with a spring or contraweight, but instead with a software setpoint. This setpoint is compared with the measured apparent weight and tells the processor (e.g., microcontroller) to command raising or lowering the displacer. As an AW setpoint, typically one can use 15 grams below the weight of the displacer in air. Most displacers produced have a standard weight, which allows using a default AW setpoint in the software.

The 15 gram AW setpoint value (or other fixed AW setpoint value) can be used to get sufficient margin with various external and internal factors including aspects such as measuring wire weight (which increases with the more wire paid out, etc.). As such the immersion depth is already kept to a minimum. But even 5 mm or 10 mm only, the effect can be noticeable (depending on the expected density changes).

However, from a legal metrology perspective a maximum permissible error of only +/-1 mm for level is typically acceptable. With 10 mm immersion 10% of density change results in a 1 mm level error. 10% typically only occurs when the product is changed, and the effect is noticeable. 1 mm is generally the level accuracy requirement for all weight and measures approved applications (i.e. where tax/duties are levied), but also for custody transfer.

Although the density changes typically can just be within the acceptable range (e.g., a typical hydrocarbon has a thermal expansion coefficient close to 0.08%/° C., product changes such as in composition (for example the Propane/Butane ratio), or the effects of weathering (maturing) LNG might just be acceptable, the changes when swapping products such as often occurs in chemical storage lease tanks can far exceed the acceptance level. Even the noticeable smaller temperature effects become an issue when displacer <90 mm are selected.

While various disclosed embodiments have been described above, it should be understood that they have been presented by way of example only, and not limitation. Numerous changes to the subject matter disclosed herein can be made in accordance with this Disclosure without departing from the spirit or scope of this Disclosure. In addition, while a particular feature may have been disclosed with respect to only one of several implementations, such feature may be combined with one or more other features of the other implementations as may be desired and advantageous for any given or particular application.

The invention claimed is:

1. A method of measuring a level of a liquid (liquid level) in a storage tank, comprising:
providing an electromechanical liquid level gauge that uses a servo principle (ESG) including a controller having a processor, a displacer having a negative buoyancy suspended on a measuring wire from a spiral grooved measuring drum for causing a torque on said drum having a servo motor with a gear (motor) coupled to rotate said drum arranged to balance a weight of said displacer, wherein a change in said liquid level causes a change in a counterforce to move said ESG out of balance;
said processor monitoring an output of a sensor that senses said torque (torque sensor) and then in response controls a movement of said motor using a programmed apparent weight set point (programmed setpoint) to raise said displacer if an apparent weight derived from said torque is too low or to lower said displacer if said apparent weight is too high to reach said programmed setpoint, said processor including an associated memory storing a density compensated essentially fixed immersion depth level gauging algorithm (algorithm), said algorithm executed by said processor implementing:
obtaining a density estimate or current measure for a density of said liquid (density reading);
using said density reading, continuously correcting an immersion depth of said displacer (immersion depth) for changes in said density to provide an essentially fixed displacer immersion depth, and
calculating said liquid level from said density reading and said immersion depth,
creating a reference buoyancy curve, and
comparing a measured current buoyancy curve to said reference buoyancy curve to determine whether said liquid is sticking to said displacer.

2. The method of claim 1, wherein said obtaining said density reading comprises obtaining said density estimate using said displacer together with Archimedes law.

3. The method of claim 1, wherein said providing further comprises providing a shape for said displacer (displacer shape), wherein said obtaining said density reading comprises submerging or raising said displacer and using said displacer shape to obtain said density estimate.

4. The method of claim 1, wherein said obtaining comprises said obtaining said current measure obtained using a Hybrid Inventory Management System (HIMS).

5. The method of claim 1, wherein said obtaining comprises obtaining said current measure and continuously updating said current measure.

6. The method of claim 1, further comprising detecting at least one abnormality in said tank from said density reading.

7. The method of claim 1, wherein said torque sensor measures said torque indirectly using a magnetic coupling.

8. An electromechanical liquid level gauge that uses servo principle (ESG), comprising:
a controller having a processor;
a displacer having a negative buoyancy in a liquid, suspended on a measuring wire from a spiral grooved measuring drum for causing a torque on said drum having a servo motor with a gear (motor) coupled to rotate said drum arranged to balance a weight of said displacer, wherein an equilibrium condition exists when said displacer is partly submerged into said liquid, wherein a change in a level of said liquid (liquid level) causes a change in a counterforce to move said ESG out of balance;
said processor monitoring an output of a sensor that senses said torque (torque sensor) and then in response controls a movement of said motor using a programmed apparent weight set point (programmed setpoint) to raise said displacer if an apparent weight derived from said torque is too low or to lower said displacer if said apparent weight is too high to reach said programmed setpoint, said processor including an associated memory storing a density compensated essentially fixed immersion depth level gauging algorithm (algorithm), said algorithm executed by said processor implementing:

obtaining a density estimate or current measure for a density of said liquid (density reading);

using said density reading, continuously correcting an immersion depth of said displacer (immersion depth) for changes in said density to provide an essentially fixed displacer immersion depth, calculating said liquid level from said density reading and said immersion depth, and comparing a measured current buoyancy curve to a stored reference buoyancy curve to detect whether said liquid is sticking to said displacer.

9. The ESG of claim 8, wherein said obtaining said density reading comprises obtaining said density estimate using said displacer together with Archimedes law.

10. The ESG of claim 8, wherein said providing further comprises providing a shape for said displacer (displacer shape), wherein said obtaining said density reading comprises submerging or raising said displacer and using said displacer shape to obtain said density estimate.

11. The ESG of claim 8, wherein said obtaining comprises obtaining said current measure and continuously updating said current measure.

12. The ESG of claim 8, wherein said torque sensor measures said torque indirectly using a magnetic coupling.

13. The ESG of claim 8, wherein said processor further implementing detecting at least one abnormality in said tank from said density reading.

* * * * *